(12) United States Patent
Horbaschek

(10) Patent No.: US 6,735,280 B2
(45) Date of Patent: May 11, 2004

(54) MEDICAL X-RAY INSTALLATION AND METHOD FOR THE OPERATION THEREOF

(75) Inventor: Heinz Horbaschek, Erlangen (DE)

(73) Assignee: Siemens Aktiengesellschaft, Münich (DE)

(*) Notice: Subject to any disclaimer, the term of this patent is extended or adjusted under 35 U.S.C. 154(b) by 104 days.

(21) Appl. No.: 10/193,590

(22) Filed: Jul. 11, 2002

(65) Prior Publication Data
US 2003/0016786 A1 Jan. 23, 2003

(30) Foreign Application Priority Data
Jul. 11, 2001 (DE) .......................... 101 33 657

(51) Int. Cl.$^7$ ................................ H05G 1/64
(52) U.S. Cl. ...................... 378/98.8; 378/205
(58) Field of Search .................. 378/98.8, 205, 378/19, 17; 250/370.09

(56) References Cited

U.S. PATENT DOCUMENTS

| | | | | |
|---|---|---|---|---|
| 4,884,293 A | | 11/1989 | Koyama | |
| 4,987,583 A | * | 1/1991 | Travanty et al. | 378/91 |
| 6,055,292 A | * | 4/2000 | Zeller et al. | 378/21 |
| 6,155,713 A | * | 12/2000 | Watanabe | 378/197 |
| 6,302,580 B1 | * | 10/2001 | Dwyer et al. | 378/197 |
| 6,334,708 B1 | * | 1/2002 | Kosugi | 378/197 |
| 6,435,716 B1 | * | 8/2002 | Polkus et al. | 378/205 |
| 6,630,676 B2 | * | 10/2003 | Takemoto | 250/370.09 |

FOREIGN PATENT DOCUMENTS

WO        WO 01/45562        6/2001

* cited by examiner

Primary Examiner—Craig E. Church
Assistant Examiner—Irakli Kiknadze
(74) Attorney, Agent, or Firm—Schiff Hardin LLP

(57) ABSTRACT

In a method for the operation of a medical X-ray installation having at least one C-arm at which a solid-state image detector is rotatably arranged and also having a control device that controls the operation thereof, whereby the control device determines an arbitrary position for the solid-state image detector relative to the C-arm, for positioning the solid-state image detector, at which the collision risk of the solid-state image detector with an object is lowest; and the image is computationally rotated dependent on the position data of the solid-state image detector after the image exposure in order to enable a perpendicular presentation of the examination region at an output medium.

18 Claims, 1 Drawing Sheet

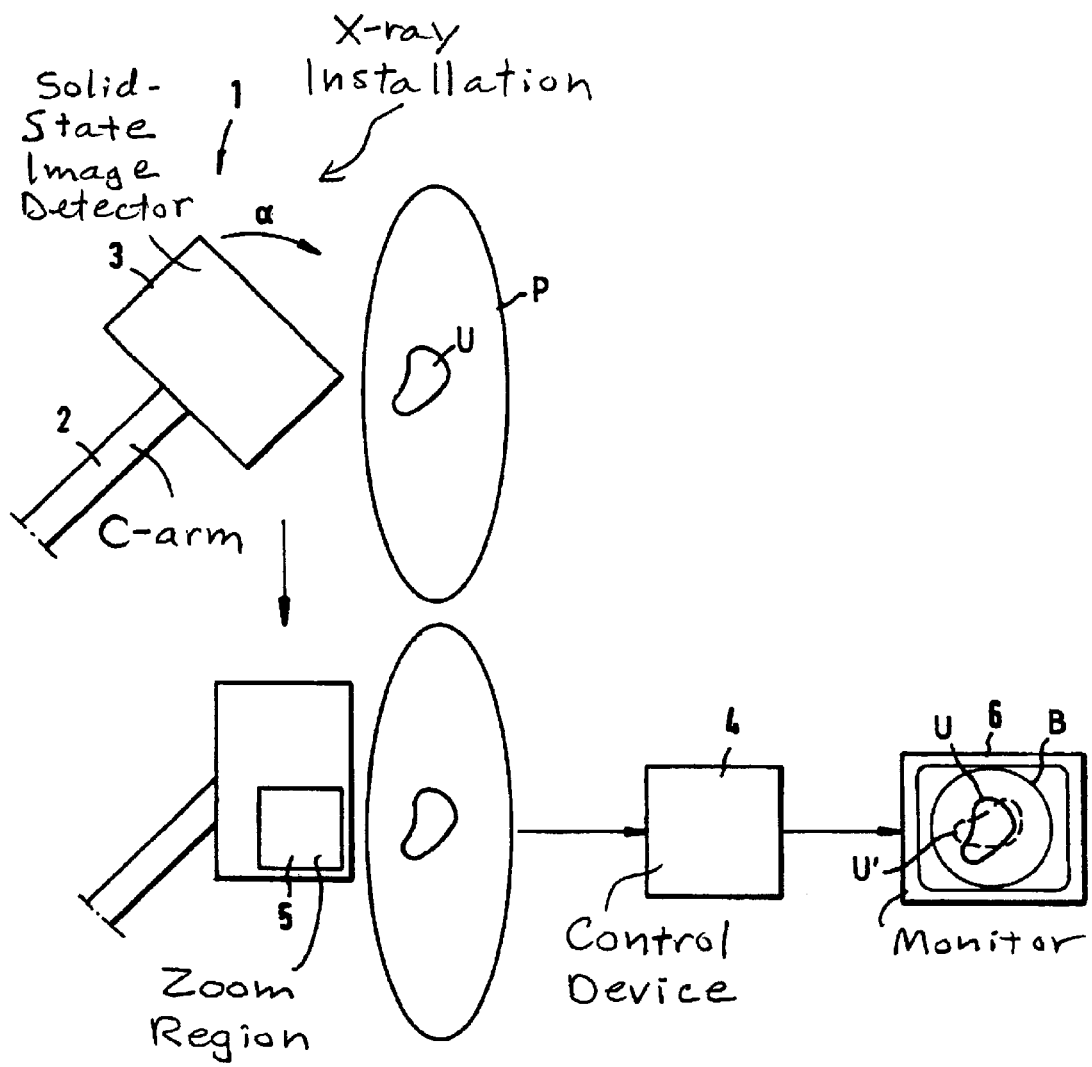

MEDICAL X-RAY INSTALLATION AND METHOD FOR THE OPERATION THEREOF

BACKGROUND OF THE INVENTION

1. Field of the Invention

The present invention is directed to a method for the operation of a medical X-ray installation of the type having at least one C-arm at which a solid-state image detector is rotatably arranged and also having a control device that controls the operation thereof.

2. Description of the Prior Art

In known X-ray installations, X-ray image intensifiers of different sizes are employed dependent on the application. In general angiography, for example, at least one X-ray image intensifier having a minimum diameter of 33 cm, preferably having a diameter of 40 cm, is necessary because of the field of view required for tracking a contrast agent bolus. In cardio-angiography, in contrast, smaller X-ray image intensifier formats such as, preferably, a 23 cm X-ray image intensifier are employed because the smaller size of the object to be image and particularly because of the high collision hazard of larger image intensifiers with the patient, for example given oblique projections. This leads to compromises in combination systems that are currently being more frequently employed. For example, a 33 cm X-ray image intensifier is actually too small for best results in general angiography; for cardio-angiography, in contrast, even the wide outside edge of the X-ray image intensifier is disturbing when, for example, a format as small as 14 cm or the 17 cm is employed.

Usually, therefore, X-ray systems employ a fixed arrangement of an X-ray tube and an image receiver wherein the spacing between these two components from one another can be variable, but the central ray always remains centered on the middle of the image receiver. In the case of slanting angulations, an image rotation may ensue, for example, by turning the video camera, so that the image remains in an upright position for the viewer.

The maximally possible projection angles are thereby predetermined by the mechanical dimensions of the components (for example, image intensifier housing). If used, possible collision protection control of the X-ray system also is matched to these fixed data.

In the case of mechanically large image receivers together with small zoom format, i.e. utilization of only a central, small region of the image receiver, a large "collar" thus arises between the outside dimensions of the detector and the edge of the utilized image. The maximum angulation thus is not determined by the edge of the utilized image but by the basic mechanical arrangement.

Further, the use of solid-state image detectors in the framework of cardio-angiography is known. An added difficulty associated with the use of solid-state detectors, however, is that the rectangular or quadratic shape is disadvantageous in angulations in the event of a collision with the patient or some other object. It has been proposed to selectively employ a large or a small solid-state image detector dependent on the application. This, however, involves complicated mechanisms and leads to unacceptable costs.

PCT Application WO 01/45562 discloses an X-ray diagnostics installation with a collision detector that generates an alarm signal when the force exerted onto the movable parts exceeds a threshold.

SUMMARY OF THE INVENTION

An object of the present invention is to provide a method with which the advantages of a solid-state detector can be maintained while still allowing operation and in the framework of cardio-angiography with a zoomed image region that is smaller compared to the entire image converter format.

In a method of the type initially described, it is inventively achieved by turning or rotating the solid-state detector into an arbitrary position relative to the C-arm for the image pickup in order to avoid a collision, the potential collision risk being minimal in this arbitrary position, and wherein the image registered with the solid-state image detector is computationally rotated dependent on the position data of the solid-state image detector in order to enable a vertical presentation of the image at an output medium.

In accordance with the invention the solid-state image detector is rotated into an arbitrary position relative to the C-arm wherein it does no collide with the patient or some third object, for example the patient support table, so that the smallest unusable edge between the outside dimensions of the detector and the image area always arises in the desired position (angulation). This is especially important in the case of non-circular detectors since, for example, a corner thereof is likely to lead to a collision. In the position employed in the inventive method, there is usually the problem in conventional systems that the registered image no longer resides perpendicularly with reference to the longitudinal axis of the patient support table, so that it is displayed in rotated fashion at a monitor due to the rotated position of the solid-state image detector. In known systems, namely, the rotation of the solid-state detector always ensues such dependent on the projection angle of the C-arm such that the image always is presented upright with reference to the longitudinal axis of the table. The invention departs from this by allowing any arbitrary detector position. In order nevertheless to arrive at the standard image presentation desired by the physician, in the inventive method the registered image is computationally rotated, so that the image can be presented perpendicularly as usual, for example at the monitor. The computational rotation ensues dependent on the position data of the solid-state image detector relative to the C-arm, since the manner by which the registered image is to be rotated can be derived therefrom. This rotation can be implemented in real time by the available high-performance digital electronics, so that no disadvantages whatsoever occur for the attending physician. Due to the possibility of being able—differing from known systems—to rotate the solid-state detector into an arbitrary position relative to the C-arm, the detector can now be set such that it does not collide with the patient or the patient table or the like, but nonetheless can be moved as close as possible to the patient. Regardless of the format of the solid-state image detector, thus, arbitrary angulations are possible with the inventive method, so that an application-dependent change of detectors can be foregone.

In a further embodiment of the inventive method for optimizing the positioning possibilities of the solid-state image detector, the control device also determines that position or attitude of the zoom region of the solid-state image detector wherein the collision risk is lowest. To that end, an image field at the edge of the detector from the full image area of the detector given zoom is always employed, so that the smallest possible distance between the current image edge and the mechanical edge of the detector always arises. According to this embodiment of the invention, thus, the zoom possibility of the solid-state image detector is also utilized within the framework of the inventive method so that the control device not only determines the optimum rotated position but also, in conjunction therewith, determines the optimum positioning of the zoom region, or links the two with each other in order to thus determine the optimum position of the two with reference to the geometry of the detector as well as the geometry of the patient. When zooming occurs, the position data of the position of the zoom region also enter into the subsequently undertaken, computational image rotation.

The inventive method can be employed both in X-ray installations with a C-arm and in bi-planar X-ray installations. In this latter instance, i.e. when two separately movable C-arms each with a solid-state image detector are provided, the position data of the other solid-state image detector can be inventively taken into consideration in the determination of the positioning of the first solid-state image detector and, of course, its zoom region. Thus, the inventive method also allows a collision-free motion of the detectors taking the respective position of the two detectors into consideration in bi-planar systems as well.

Inventively, relevant data can be supplied by one or more collision sensors or by a collision calculation program in order to determine the position data of the solid-state image detector and of the zoom region.

The invention also is directed to a medical X-ray installation having at least one C-arm at which a solid-state image detector is rotatably arranged as well as having a control device. In accordance with the invention the control device of the X-ray installation is fashioned for determining that position of the solid-state image detector lying arbitrarily relative to the C-arm wherein the collision risk of the solid-state detector with an image object is at its lowest, and the control device also is fashioned for rotating the image registered with the solid-state image detector such that the image of the examination region can be displayed in a vertical position at an output medium.

In an embodiment of the inventive X-ray installation, the control device also determines the position of the zoom region of the solid-state image detector wherein the collision risk of the solid-state image detector with a third object is lowest, with the respective positions of the solid-state image detector and the zoom region of the detector being referred to one another in this case, so that a position that is as close as possible relative to the patient can be achieved overall.

Further, a number of collision sensors can be provided in the inventive X-ray installation, these supplying data relevant for the determination of the positions of the solid-state image detector and, possibly, of the zoom region. Alternatively, a calculation program can be used for supplying data relevant for the determination of the position data of the solid-state image detector and, possibly, of the zoom region.

The X-ray installation can be a bi-planar installation, wherein the control device is fashioned for the determination of the position data of one solid-state image detector and of its appertaining zoom region dependent at least on the position data of the other solid-state image detector.

DESCRIPTION OF THE DRAWINGS

The single FIGURE is a schematic illustration of an X-ray installation constructed and operating in accordance with the principles of the present invention.

DESCRIPTION OF THE PREFERRED EMBODIMENTS

The inventive X-ray installation 1, which is shown only in a schematic excerpt has a C-arm 2 at which a solid-state image detector 3 is arranged. Of course, an X-ray source is provided at the other end of the C-arm 2, this not being shown in detail here since it is not important to the inventive improvement. An examination region U of a patient P is to be registered with the X-ray installation 1. The examination region U, for example, contains the coronary vessels of the patient P. In order to place the solid-state image detector 3 as close as possible to the examination region, the detector 3—as shown in the upper part of the figure—is rotated by an angle a relative to the C-arm 2 into an arbitrary position. This position was computationally determined with the control device 4. The computation is made with at least one criterion being that the collision risk of the solid-state image detector with the patient P or some other, third object that is not shown is minimal in this position. Simultaneously, the zoom region 5 of the solid-state image detector is positioned and displaced toward the edge, likewise on the basis of computational position and attitude determination by the control device 4, such that the solid-state image detector can be optimally positioned relative to the patient P, or the examination region U of the patient P. If the solid-state image detector 3 has a stray radiation grid, the zoom region 5 can be displaced only in one direction perpendicular to the direction of the absorption lamellae of the stray radiation grid. If no stray radiation grid is employed, then the zoom region 5 can be arbitrarily positioned, i.e. can also be displaced all the way into a corner.

The image B is displayed at a presentation medium, such as a monitor 6. As a result of the rotation of the solid-state image detector 3, the image B at the monitor 6 now no longer resides upright with reference to the longitudinal axis of the patient table (not shown) as usual, but at an angle thereto. Consequently, the image B and, thus, the examination region would be presented in rotated fashion, as indicated by the broken-line examination region U'. In order to avoid this, the examination region or the image U is computationally, electronically rotated back into the perpendicular, customary position after the image exposure, as shown by the solid-line examination region U in the FIGURE. If the image were quadratically presented, then a skewed presentation of the image—wherein the examination region in fact resides perpendicularly but the image edges lie turned—would occur after the back-rotation. In order to avoid this optically unpleasant presentation, the image B is expediently presented with a circular edge limitation.

The inventive method as well as the inventive X-ray installation allow an optimized positioning of the solid-state image detector while simultaneously obtaining the image presentation to which the physician is accustomed. This is enabled by the possibility of being able to arbitrarily position the solid-state image detector and to displace and position the zoom region as needed, connected with the possibility of electronically rotating the image back into the customary position for the image display. As a result, only the slight mechanical edge of the solid-state image detector remains effective, even given zoom, so that the active area of the solid-state image detector can be optimally utilized, and the situation for every solid-state image detector format is significantly better than in the known X-ray image intensifier zoom, wherein the effective edge already amounts to several centimeters given full format and amounts to significantly more in the case of zoom. Arbitrary angulations therefore are possible with the inventive method and the inventive X-ray installation regardless of the format of the solid-state image detector, so that an application-dependent change of detectors can be foregone.

The inventive method thus yields a lower collision hazard, even in the case of large detectors, than in the case of an adapted X-ray image intensifier system and zoom.

The inventive method does not require modification of known mechanical and electronic collision protection devices and controls. This remains functionally in place; but modified reference values are employed as a result of the detector rotation and the non-centric zoom.

Without the inventive method, a large detector—first due to is polygonal shape (semiconductor detector) and particularly given small zoom formats—would involve considerable limitations in examinations wherein it is not normally standard to employ small zoom formats (cardio-angio).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a medical X-ray installation having a support at which a solid-state image detector is rotatably mounted and having a control device which controls positioning of said solid-state image detector on said support, said method comprising the steps of:

determining an arbitrary position of said solid-state image detector relative to said support at which a risk of collision of said solid-state image detector with another object is lowest, and positioning said solid-state image detector on said support at said arbitrary position;

irradiating said solid-state image detector with X-rays during an exposure to obtain an X-ray image from said solid-state image detector; and after said exposure, computationally rotating said image dependent on said arbitrary position of said solid-state image detector to enable a perpendicular presentation of an examination region contained in said X-ray image at an output medium.

2. A method as claimed in claim 1 wherein the step of irradiating said solid-state image detector with X-rays during an exposure to obtain an X-ray image from said solid-state image detector comprises obtaining an image of a zoom region of said solid-state image detector, and wherein the step of determining said arbitrary position of said image detector comprises determining a position of said zoom region of said solid-state image detector wherein said risk of collision of said solid-state image detector with an object is lowest.

3. A method as claimed in claim 2 comprising additionally rotating said image dependent on said arbitrary position of said zoom region.

4. A method as claimed in claim 1 wherein said support is a first support and wherein said solid-state image detector is a first solid-state image detector, and wherein said medical X-ray installation further has a second support at which a second solid-state image detector is rotatably mounted and wherein the step of determining said arbitrary position of said first solid-state image detector includes determining said arbitrary position of said first solid-state image detector dependent, at least in part, on a position of said second solid-state image detector.

5. A method as claimed in claim 4 wherein the step of irradiating said solid-state image detector with X-rays during an exposure to obtain an X-ray image from said solid-state image detector comprises obtaining an image of a zoom region of said solid-state image detector, and wherein the step of determining said arbitrary position of said image detector comprises determining a position of said zoom region of said solid-state image detector wherein said risk of collision of said solid-state image detector with an object is lowest, also dependent on said position of said second solid-state image detector.

6. A method as claimed in claim 1 comprising the additional step of obtaining position data identifying a position of said solid-state image detector for use in determining said arbitrary position of said solid-state image detector.

7. A method as claimed in claim 6 wherein the step of irradiating said solid-state image detector with X-rays during an exposure to obtain an X-ray image from said solid-state image detector comprises obtaining an image of a zoom region of said solid-state image detector, and wherein the step of determining said arbitrary position of said image detector comprises determining a position of said zoom region of said solid-state image detector, dependent in part on said position data, wherein said risk of collision of said solid-state image detector with an object is lowest.

8. A method as claimed in claim 1 comprising determining said arbitrary position of said solid-state image detector using a collision calculation program.

9. A method as claimed in claim 8 wherein the step of irradiating said solid-state image detector with X-rays during an exposure to obtain an X-ray image from said solid-state image detector comprises obtaining an image of a zoom region of said solid-state image detector, and wherein the step of determining said arbitrary position of said image detector comprises determining a position of said zoom region of said solid-state image detector wherein said risk of collision of said solid-state image detector with an object is lowest using said collision calculation program.

10. A medical x-ray installation comprising:

a support and a solid-state image detector rotatably mounted on said support; and a control device for controlling positioning of said solid-state image detector relative to said support, said control device being programmed to determine an arbitrary position of said solid-state image detector relative to said support wherein a risk of collision of said solid-state image detector with an object is lowest, and to rotate an image obtained upon irradiation of said solid-state image detector with X-rays so that said image presents an examination region in a perpendicular presentation.

11. An X-ray installation as claimed in claim 10 wherein said support is a C-arm.

12. An X-ray installation as claimed in claim 10 wherein said solid-state image detector has a zoom region, and wherein said control device determines a position of said zoom region of said solid-state image detector at which a risk of collision of said solid-state image detector with an object is lowest.

13. An X-ray installation as claimed in claim 10 further comprising at least one collision sensor which generates position data supplied to said control unit, and wherein said control unit employs said position data for determining said arbitrary position of said solid-state image detector.

14. An X-ray installation as claimed in claim 13 wherein said solid-state image detector has a zoom region, and wherein said control device determines a position of said zoom region of said solid-state image detector, dependent at least in part on said position data, at which a risk of collision of said solid-state image detector with an object is lowest.

15. An X-ray installation as claimed in claim 10 wherein said control device employs a collision calculation program for determining said arbitrary position of said solid-state image detector.

16. An X-ray installation as claimed in claim 15 wherein said solid-state image detector has a zoom region, and wherein said control device determines a position of said zoom region of said solid-state image detector at which a risk of collision of said solid-state image detector with an object is lowest using said collision calculation program.

17. An X-ray installation as claimed in claim 10 wherein said support is a first support and wherein said solid-state image detector is a first solid-state image detector, and further comprising a second support on which a second solid-state image detector is rotatably mounted, and wherein said control device determines said arbitrary position of said first solid-state image detector dependent, at least in part, on a position of said second solid-state image detector.

18. An X-ray installation as claimed in claim 17 wherein said first solid-state image detector has a zoom region, and wherein said control device determines a position of said zoom region of said first solid-state image detector at which a risk of collision of said solid-state image detector with an object is lowest dependent at least in part on said position of said second solid-state detector.

* * * * *